United States Patent
Tsukamoto et al.

(10) Patent No.: US 6,596,439 B1
(45) Date of Patent: Jul. 22, 2003

(54) LITHIUM ION BATTERY CAPABLE OF BEING DISCHARGED TO ZERO VOLTS

(75) Inventors: Hisashi Tsukamoto, Saugus, CA (US); Clay Kishiyama, Burbank, CA (US); Mikito Nagata, Valencia, CA (US); Hiroshi Nakahara, Santa Clarita, CA (US); Tiehua Piao, Saugus, CA (US)

(73) Assignee: Quallion LLC, Sylmar, CA (US)

(*) Notice: Subject to any disclaimer, the term of this patent is extended or adjusted under 35 U.S.C. 154(b) by 0 days.

(21) Appl. No.: 09/675,287

(22) Filed: Sep. 29, 2000

Related U.S. Application Data
(60) Provisional application No. 60/199,895, filed on Apr. 26, 2000.

(51) Int. Cl.$^7$ .............................. H01M 4/52; H01M 4/66
(52) U.S. Cl. .................... 429/245; 429/223; 429/231.3; 429/231.95
(58) Field of Search .......................... 429/221, 231.95, 429/245, 223, 231.3

(56) References Cited

U.S. PATENT DOCUMENTS

| | | | |
|---|---|---|---|
| 4,092,464 A | * 5/1978 | Dey | ............. 429/127 |
| 4,935,316 A | 6/1990 | Redey | |
| 5,264,201 A | * 11/1993 | Dahn | ............. 423/594 |
| 5,278,000 A | 1/1994 | Huang et al. | |
| 5,411,537 A | * 5/1995 | Munshi | ............. 607/33 |
| 5,478,674 A | 12/1995 | Miyasaka | |
| 5,500,583 A | 3/1996 | Buckley et al. | |

(List continued on next page.)

FOREIGN PATENT DOCUMENTS

| | | |
|---|---|---|
| JP | 01-006384 A2 | 1/1989 |
| JP | 01-014881 A2 | 1/1989 |
| JP | 64-002258 A2 | 1/1989 |
| JP | 02-174070 A2 | 7/1990 |
| JP | 03-192663 A2 | 8/1991 |
| JP | 05-047369 A2 | 2/1993 |
| JP | 05-047384 A2 | 2/1993 |

(List continued on next page.)

OTHER PUBLICATIONS

K. Colbow et al., Structure and Electrochemistry of the Spinal Oxides $LiTi_2O_4$ and $Li_{4/3}Ti_{5/3}O_4$, Journal of Power Sources, 1989, pp. 397–402, vol. 26.

D. Linden, Handbook of Batteries, $2^{nd}$ Ed., Copyright 1995 by McGraw–Hill, Inc., New York, pp. 36.4–36.17 (See especially Fig. 36.2).

P. Dan et al., More Details on the New $LiMnO_2$ Rechargeable Battery Technology Developed at Tadiran, Journal of Power Sources, 1997, pp., 443–447, vol. 68.

M. Broussely et al., Lithium Insertion Into Host Materials: The Key To Success For Li Ion Batteries, Electrochimica Acta, 1999, pp. 3–22, vol. 45 (See generally; esp. Fig. 1).

H. Tsukamoto, Synthesis and Electrochemical Studies of lithium transition metal oxides for lithium–ion batteries, Department of Chemistry, University of Aberdeen, 1999 (See table 1; Fig. 1–6).

Y. Lee et al., Synthesis and Electrochemical Characterization of Orthorhombic $LiMnO_2$ Material, Department of Applied Chemistry, Saga University, honjo 1, Saga 840–8502, Japan (1 page).

*Primary Examiner*—Mark Ruthkosky
(74) *Attorney, Agent, or Firm*—M. Elizabeth Bush

(57) ABSTRACT

A lithium ion battery particularly configured to be able to discharge to a very low voltage, e.g. zero volts, without causing permanent damage to the battery. More particularly, the battery is configured to define a Zero Volt Crossing Potential (ZCP) which is lower than a Substrate Dissolution Potential (SDP) to thus avoid low voltage substrate damage. The configuration includes a lithium nickel cobalt oxide positive active material combined with negative electrode comprising a titanium or titamum alloy substrate having a carbon active material formed thereon.

27 Claims, 7 Drawing Sheets

U.S. PATENT DOCUMENTS

| | | | |
|---|---|---|---|
| 5,578,398 A | * 11/1996 | Jenkins | 429/233 |
| 5,591,546 A | 1/1997 | Nagaura | |
| 5,614,331 A | * 3/1997 | Takeuchi | 429/9 |
| 5,631,100 A | * 5/1997 | Yoshino | 429/62 |
| 5,783,333 A | * 7/1998 | Mayer | 429/223 |
| 5,828,202 A | * 10/1998 | Tamai | 320/141 |
| 6,017,654 A | * 1/2000 | Kumta | 429/231.95 |
| 6,159,636 A | * 12/2000 | Wang | 429/223 |
| 6,181,105 B1 | 1/2001 | Cutolo et al. | |
| 6,204,634 B1 | 3/2001 | Zimmerman et al. | |
| 6,207,326 B1 | 3/2001 | Kawakami et al. | |
| 6,245,464 B1 | 6/2001 | Spillman et al. | |
| 2002/0076612 A1 | 6/2002 | Tanizaki et al. | |

FOREIGN PATENT DOCUMENTS

| | | | | |
|---|---|---|---|---|
| JP | 05-074462 A2 | 3/1993 | | |
| JP | 5074462 | * 3/1993 | | H01M/4/64 |
| JP | 05-151995 A2 | 6/1993 | | |
| JP | 05-174872 A2 | 7/1993 | | |
| JP | 05-325968 A2 | 12/1993 | | |
| JP | 5325968 | * 12/1993 | | H01M/4/58 |
| JP | 06-203829 A2 | 7/1994 | | |
| JP | 6203829 | * 7/1994 | | H01M/4/02 |
| JP | 06-349493 A2 | 12/1994 | | |
| JP | 07-335263 A2 | 12/1995 | | |
| JP | 08-022841 A2 | 1/1996 | | |
| JP | 08-185851 A2 | 7/1996 | | |
| JP | 08-222272 A2 | 8/1996 | | |
| JP | 11-288704 A2 | 10/1999 | | |
| JP | 200260475 A2 | 9/2000 | | |
| WO | WO 00/50925 A1 | 10/1999 | | |
| WO | WO 01/82398 A1 | 11/2001 | | |

\* cited by examiner

|   | Positive Active Material | Negative Substrate Material | Temperature | Result |
|---|---|---|---|---|
| (1) | LiCoO$_2$ | Copper | 25 °C | Fail; 79.9% Retention |
|     |           |        | 37 °C | Fail; 76.2% Retention |
| (2) | LiCoO$_2$ | Titanium | 25 °C | Pass; 98.6% Retention |
|     |           |          | 37 °C | Fail; 73.5% Retention |
| (3) | LiNiCoO$_2$ | Copper | 25 °C | — |
|     |             |        | 37 °C | Fail; 90% Retention |
| (4) | LiNiCoO$_2$ | Titanium | 25 °C | — |
|     |             |          | 37 °C | Pass; 98.8% Retention |

Figure 5

LITHIUM ION BATTERY CAPABLE OF BEING DISCHARGED TO ZERO VOLTS

RELATED APPLICATIONS

This application claims the benefit of U.S. Provisional Application 60/199,895 filed Apr. 26, 2000.

FIELD OF THE INVENTION

This invention relates generally to rechargeable batteries and more particularly to a rechargeable lithium battery capable of discharging to zero volts without causing damage to the battery.

BACKGROUND OF THE INVENTION

Rechargeable lithium batteries are widely discussed in the literature and are readily commercially available. They typically consist of a positive electrode and a negative electrode spaced by a separator, an electrolyte, a case, and feedthrough pins respectively connected to the electrodes and extending externally of the case. Each electrode is typically formed of a metal substrate that is coated with a mixture of an active material, a binder, and a solvent. In a typical battery design, the electrodes comprise sheets which are rolled together, separated by separator sheets, and then placed in a prismatic case. Positive and/or negative feed through pins (i.e., terminals) are then connected to the respective electrodes and the case is sealed.

The negative electrode is typically formed of a copper substrate carrying graphite as the active material. The positive electrode is typically formed of an aluminum substrate carrying lithium cobalt dioxide as the active material. The electrolyte is most commonly a 1.1 mixture of EC:DEC in a 1.0 M salt of $LiPF_6$. The separator is frequently a micro porous membrane made of a polyolefin, such as a combination of polyethylene and/or polypropylene which can, for example, be approximately 25 $\mu$m thick.

It is typical to use protection circuitry with lithium ion batteries to avoid potential deleterious effects. Thus, protection circuitry is frequently employed to terminate charging if the voltage or temperature of the battery(or any cell) exceeds a certain level. Moreover, it is common to incorporate a low voltage cutoff to disconnect the battery from its load if the voltage of the battery (or any cell) falls below a certain lower level. This latter precaution is taken to prevent permanent damage to the battery which can occur if a voltage greater than a Damage Potential Threshold (DPT) is applied to one of the electrodes. For example, corrosion or decomposition of the negative electrode substrate can occur if a voltage greater than a Substrate Dissolution Potential (SDP) is applied to the negative electrode.

SUMMARY OF THE INVENTION

The present invention is directed to a rechargeable lithium ion battery particularly configured to be able to discharge to a very low voltage, e.g. zero volts, without causing permanent damage to the battery. More particularly, a battery in accordance with the invention is configured to define a Zero Volt Crossing Potential (ZCP) which is lower than the battery's Damage Potential Threshold (DPT) and more specifically its Substrate Dissolution Potential (SDP), to thus avoid low voltage substrate damage.

The ZCP refers to the voltage of each of the electrodes relative to a lithium reference (Li/Li+) when the battery potential, i.e., the potential between the electrodes, is zero. The SDP refers to the dissolution potential of the negative electrode substrate relative to the lithium reference (Li/Li+). A conventional lithium ion battery typically exhibits a ZCP of about 3.6 volts which can slightly exceed the battery's SDP.

In accordance with the present invention, the material selected for the negative electrode substrate has a dissolution potential greater than the ZCP. Commercially pure titanium and titanium alloys are preferred. Nickel, nickel alloys, and stainless steel can also be used.

In the normal operation of a lithium ion battery, a solid electrolyte interface (SEI) layer, i.e., a passivation layer, is formed on the negative electrode, attributable to a reaction between the negative electrode and the electrolyte. The SEI layer comprises an insulating membrane that tends to inhibit the continuing reaction of the negative electrode and electrolyte. It has been recognized that this SEI layer can dissolve at a voltage above a certain level, i.e., Film Dissolution Potential (FDP), which can lead to permanent damage to the negative electrode. In accordance with a preferred embodiment of the invention, the battery is configured to assure a ZCP lower than said FDP.

A battery's ZCP level relative to the lithium reference is dependent in part on the materials used for the positive and/or negative electrodes. In accordance with a preferred embodiment of the invention, a positive electrode active material, e.g., $LiNi_xCo_{1-x}O_2$ ($0<x\leq1$) is selected which exhibits a discharge curve appropriate to achieve a relatively low ZCP level. This feature of the preferred embodiment facilitates the implementation of a battery in accordance with the invention characterized by a Zero Crossing Potential (ZCP) less than its Substrate Dissolution Potential (SDP) and/or its Film Dissolution Potential (FDP).

Batteries in accordance with the present invention are particularly suited for use in critical applications where physical access to the battery may be difficult. For example, batteries in accordance with the invention find application in medical devices configured to be implanted under the skin in a patient's body. Such a medical device is typically comprised of a hermetically sealed housing formed of biocompatible material and dimensioned sufficiently small as to be able to be implanted without interfering with normal bodily function. A battery in accordance with the invention includes a case configured for mounting in the device housing. The battery case can be of a variety of shapes, e.g., prismatic or cylindrical, and typically defines a volume of between 0.05 cc and 30 cc. Batteries within this range exhibit capacities between 1.0 milliamp hours and 3 amp hours. An exemplary battery for use in such a device includes a prismatic hermetically sealed battery casing having dimensions of 35 mm×17 mm×5.5 mm. The device is intended to be implanted in the lower back region to help alleviate back pain using neurostimulation techniques.

BRIEF DESCRIPTION OF THE DRAWINGS

The above and other features and uniqueness of the invention will be better visualized from the following drawings and schematics.

FIG. 5 is a table showing preliminary test results of various battery configurations in accordance with the present invention.

DETAILED DESCRIPTION

The following description discloses presently contemplated preferred embodiments for practicing the invention. This description is not to be taken in a limited sense, but is offered for the purpose of describing the preferred modes of the invention. The scope of the invention should be determined with reference to the claims.

Figure 1A:
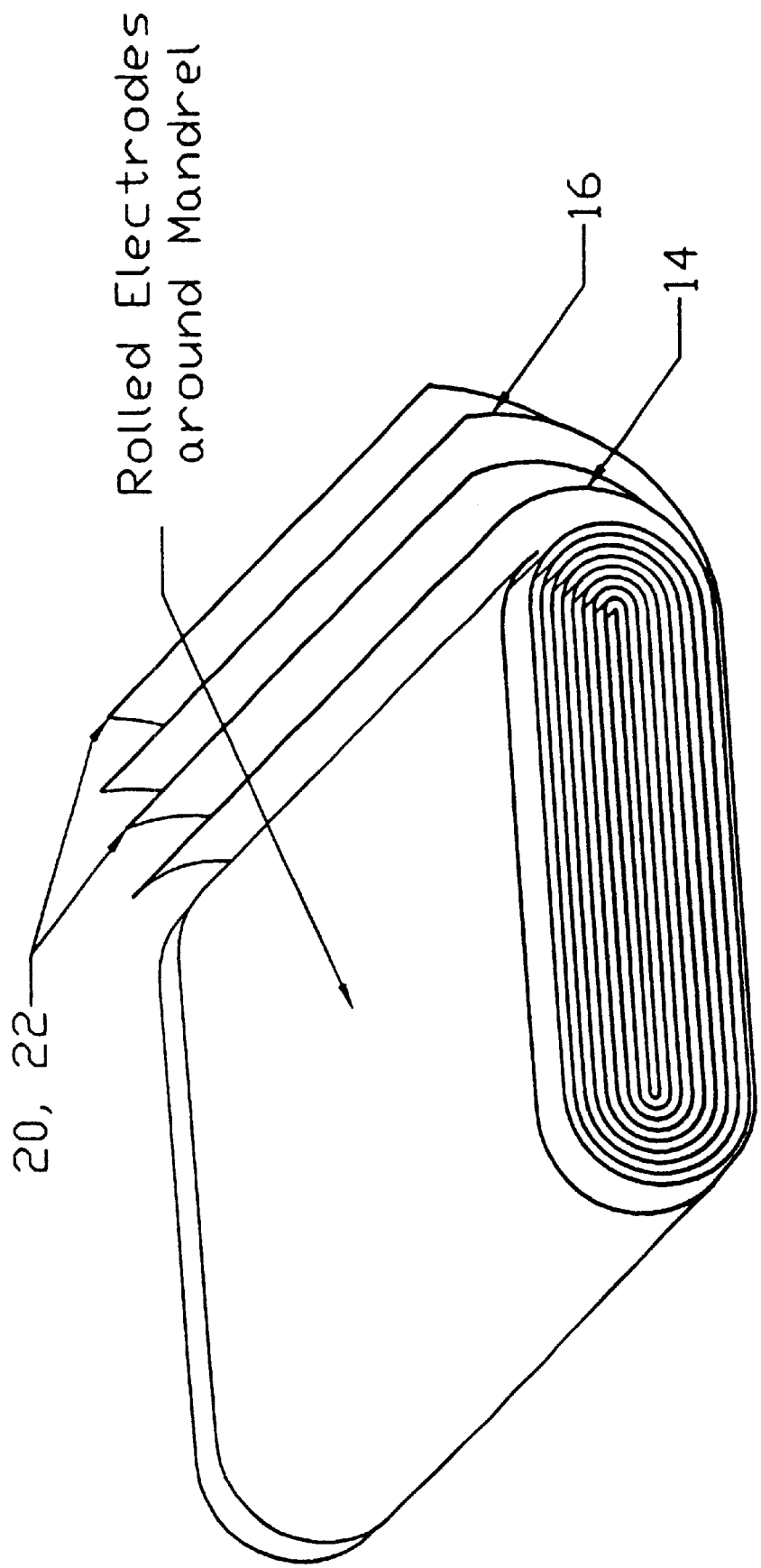
FIG. 1A schematically depicts positive and negative battery electrodes rolled around a mandrel for placement in a battery case and FIG. 1B depicts in cross-section a complete battery.
Figure 1B:
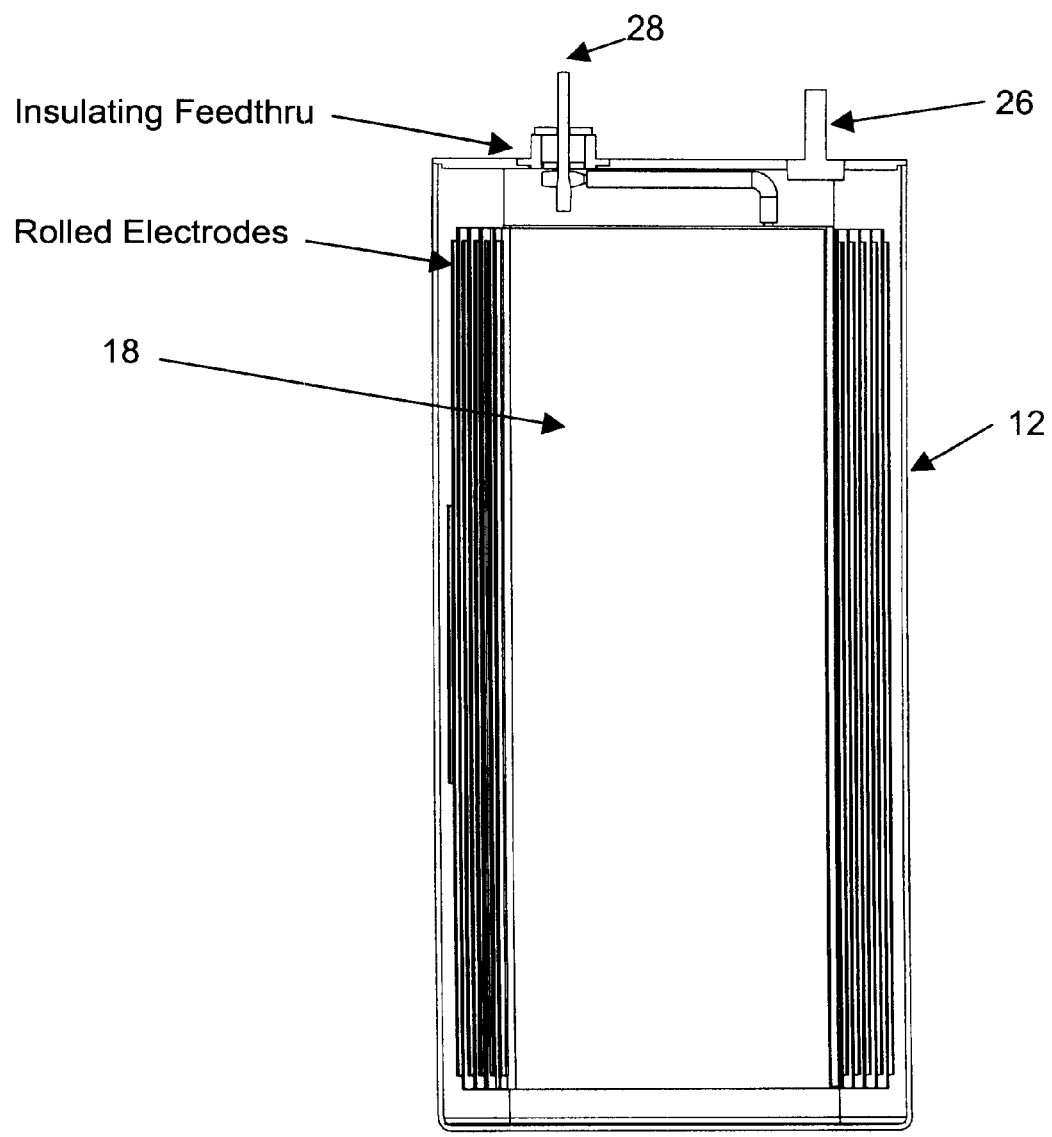

FIGS. 1A and 1B schematically depicts a typical lithium ion battery construction 10 comprising a prismatic case 12 containing a positive electrode 14 and a negative electrode 16, rolled around a mandrel 18. Separator sheets 20, 22 are incorporated in the rolling to electrically separate the electrodes. The case 12 also typically includes electrolyte material (not shown) and positive and negative feed through pins (i.e., terminals) 26, 28 which are respectively connected to the electrodes 14,16 and extend externally of the case 12.

The positive electrode 14 is typically comprised of a thin metal substrate, e.g., aluminum, carrying a layer of positive active material, e.g., lithium cobalt dioxide $LiCoO_2$ mixed with a binder, and coated on both faces of the substrate. The negative electrode 16 is typically comprised of a thin metal substrate, e.g., copper, carrying a layer of negative active material, e.g., graphite coated on both faces of the substrate.

Two layers of separator 20, 22 electrically separate the electrodes 14,16 from each other, enabling the electrodes to be rolled around mandrel 18. Each separator layer can comprise a micro porous membrane made of a combination of polypropylene and is approximately 25 μm thick. The electrolyte is most commonly a 1:1 mixture of EC:DEC in a 1.0 M salt of $LiPF_6$.

Figure 2:
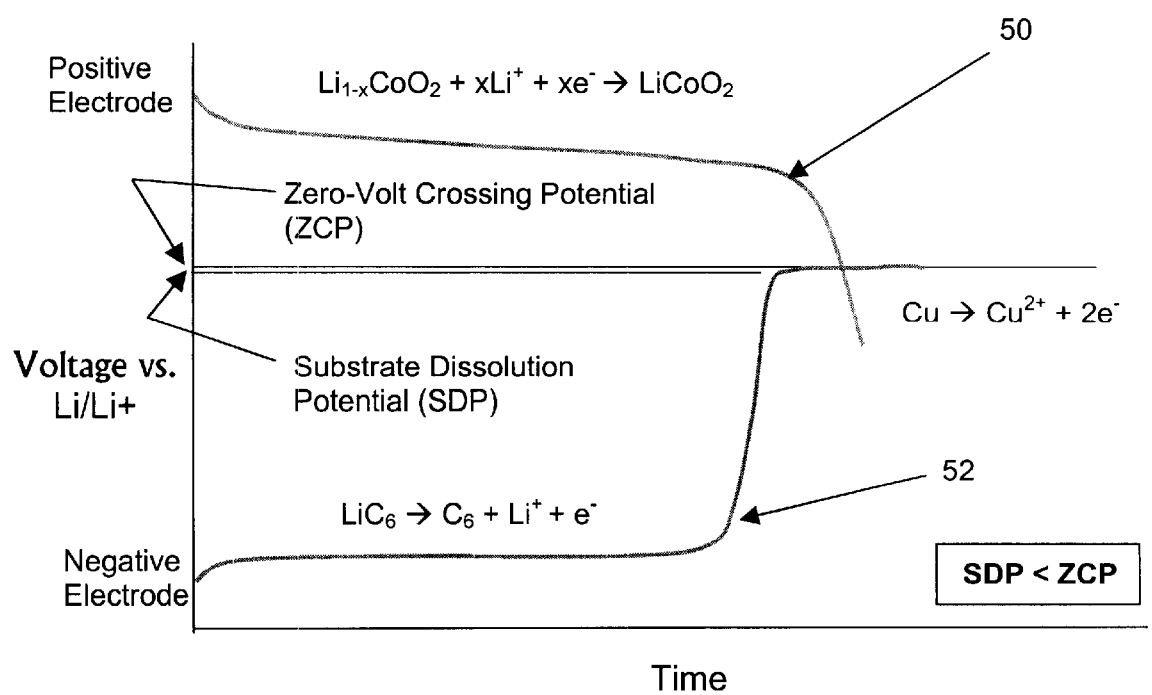
FIG. 2 shows a typical deep discharge curve for a conventional lithium ion battery using copper as the negative electrode substrate and lithium cobalt dioxide $LiCoO2$ as the positive electrode active material.

FIG. 2 shows typical deep discharge performance curves for a conventional lithium ion battery. The y-axis represents voltage relative to a lithium reference (Li/Li+) or counter electrode and the x-axis represents time. Curves 50 and 52 respectively depict the discharge curves for the positive and negative electrodes. The battery output voltage is the difference between the positive electrode voltage and the negative electrode voltage. During discharge, the positive electrode voltage decreases relative to Li/Li+ and the negative voltage increases, primarily near the end of discharge. Typically, a protection or management circuit stops the discharge when the battery voltage reaches 2.5 Volts. If the management circuit does not stop the discharge, the negative electrode potential will rise until it reaches the potential of the positive electrode which constitutes the Zero Volt Crossing Potential (ZCP) and is typically about 3.6 volts in conventional lithium ion battery constructions. The negative electrode potential at ZCP, relative to Li/Li+, can exceed the dissolution potential of the negative electrode substrate (SDP), e.g., 3.3 volts for copper, and cause dissolution and permanent damage to the substrate. The present invention is directed to battery improvements to assure that the value of SDP is greater than the value of ZCP, as represented in FIG. 3.

Figure 3:
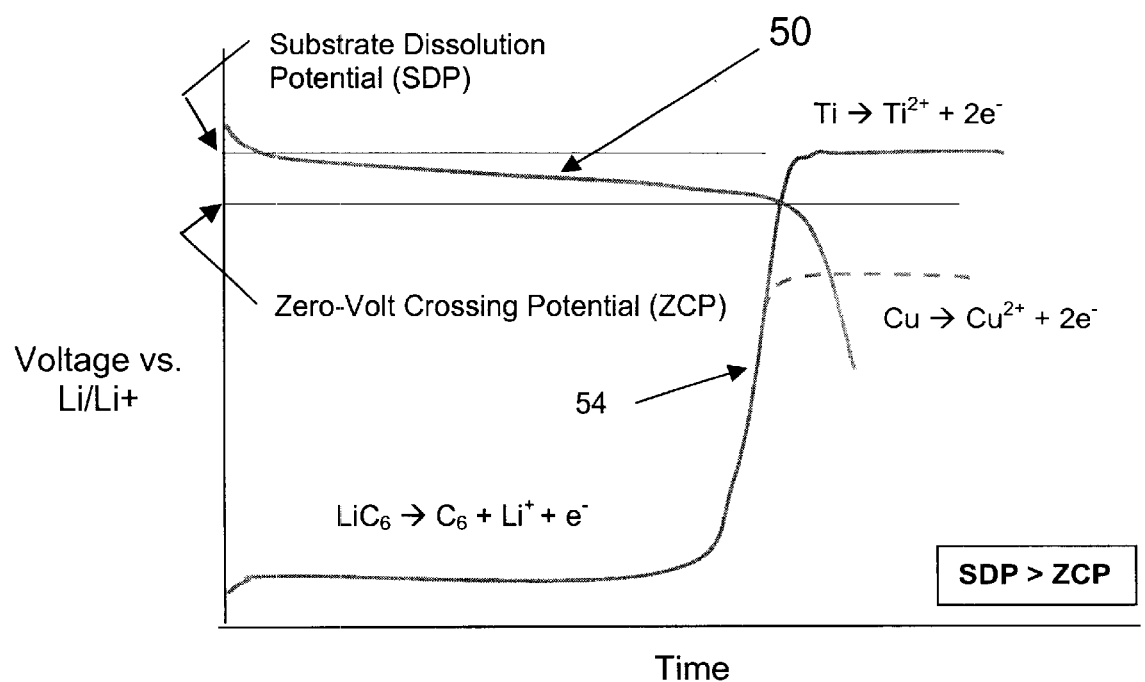
FIG. 3 shows a typical deep discharge curve for a zero volt battery in accordance with the present invention using titanium as the negative electrode substrate.

FIG. 3 depicts deep discharge performance curves for a lithium ion battery in accordance with the present invention in which the negative electrode substrate is formed of titanium instead of copper. The use of titanium increases the knee of the negative electrode curve 54 to position the SDP above the ZCP. This relationship considerably reduces potential damage to the negative electrode substrate. In addition to commercially pure titanium, i.e., titanium CP, other materials can be used to raise the SDP sufficiently, e.g. titanium alloys, nickel, nickel alloys, and stainless steel.

FIG. 3 demonstrates how the SDP level can be increased relative to the ZCP by proper choice of the negative electrode substrate material. Alternatively, or additionally, the ZCP level can be decreased relative to the SDP by proper choice of the positive electrode active material, as depicted in FIG. 4.

Figure 4:
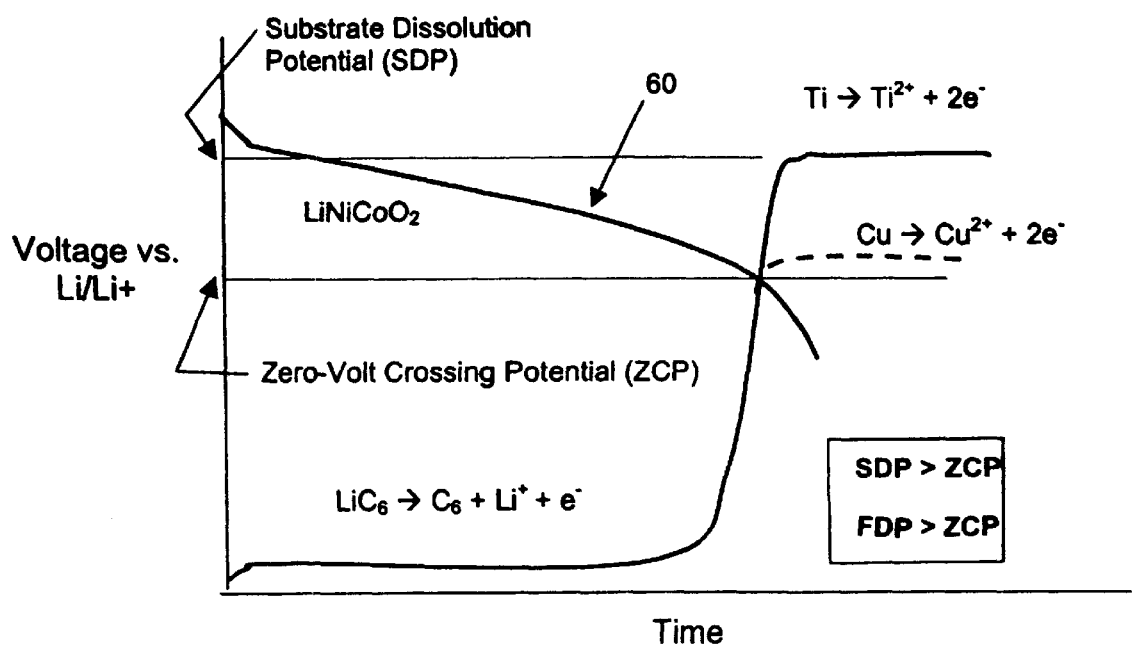
FIG. 4 shows a typical deep discharge curve for a zero volt battery in accordance with the present invention using $LiNi_xCo_{1-x}O_2$ (0<x<1) as the positive electrode active material.

More particularly, FIG. 4 shows the discharge curve 60 for a positive electrode using lithium nickel cobalt dioxide $LiNi_xCo_{1-x}O_2$ (where $0<x\leq1$) as the active material, i.e., as the intercalation compound. Note that the curve of FIG. 4 exhibits a greater negative slope than the analogous curve 50 of FIG. 2 representing the standard intercalation compound $LiCoO_2$. The effect of the increased negative slope is to lower the ZCP level relative to the lithium reference and the SDP. As was the case in connection with FIG. 3, this reduces the potential damage to the negative electrode substrate. Additionally, however, the ZCP level also falls below a Film Dissolution Potential (FDP) which is the voltage above which a solid electrolyte interface (SEI) layer begins to dissolve. The SEI, or film, comprises a passivation layer which forms on the negative electrode and functions to inhibit a continuing reaction between the negative electrode active material and the electrolyte. Dissolution of the SEI can noticeably damage the negative electrode active material.

Experiments have been performed at two different temperatures employing the aforedescribed techniques depicted in FIGS. 3 and 4. The preliminary results are summarized in the table of FIG. 5. Four different battery configurations were constructed as shown. Configuration (1) corresponds to the conventional arrangement represented in FIG. 2 comprising a copper substrate for the negative electrode and $LiCoO_2$ for the positive active material. The battery was built and then recycled once to get an initial capacity measurement. The battery was then shorted between the positive and negative leads to achieve a zero volt state. This zero volt condition was held for one week and then recharged and discharged to get a capacity measurement after zero-volt storage. The capacity retention is calculated by dividing the discharge capacity after zero volt storage by the initial capacity and multiplying by 100%. In this manner, this percentage reflects any damage that had occurred to the battery while in the zero volt state.

As represented in FIG. 5, the capacity retention for battery configuration (1) is below 80%, thus suggesting that damage had been done to the battery. After opening the battery and examining the electrodes, it was seen that copper dissolution had occurred. This battery (1) configuration performed poorly at both temperature settings.

The battery configuration (2) used $LiCoO_2$ as the positive active material and a titanium substrate as the negative substrate corresponding to the arrangement represented in FIG. 3. The results show that at 25° C. the capacity retention was at about 98% after the zero volt condition. However, at a higher temperature (37° C.), performance deteriorates to below 80%. This suggests that perhaps the zero volt crossing potential was sufficiently below SDP to avoid substrate dissolution but still high enough to exceed FDP and cause damage to the negative electrode active material. Accordingly, attempts were made to lower ZCP further to avoid damage both to the negative active material and the negative electrode substrate.

The battery configuration (3) utilizes $LiNi_xCo_{1-x}O_2$ ($0<x\leq1$) as the positive active material with copper negative electrode substrate. The results show that at 37° C. the capacity retention is quite high at 90%. However, examination after the test, revealed that some copper dissolution occurred. Battery configuration (4) uses both $LiNi_xCo_{1-x}O_2$ ($0<x\leq1$) as the positive active material and the titanium as the negative electrode substrate material. Results show that this configuration gives the best capacity retention after zero volt storage.

From the foregoing table (FIG. 5), it appears that a performance gain is achieved by configuration (2) using a titanium negative electrode substrate and by configuration (3) using lithium nickel cobalt dioxide as the positive active material. However, maximum performance gain appears in configuration (4) which combines both of these features.

Figure 6:
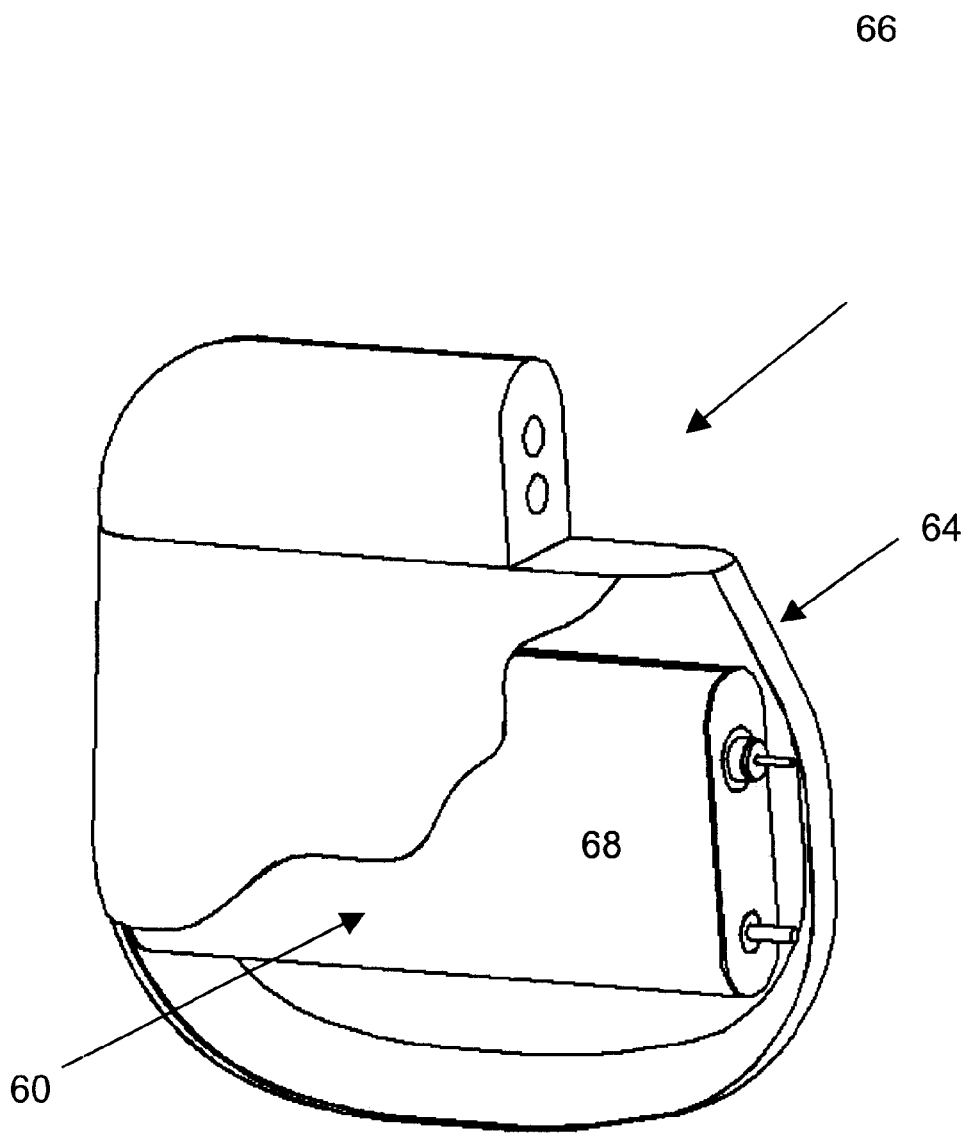
FIG. 6 schematically depicts a battery in accordance with the invention contained within an implantable medical device housing.

FIG. 6 schematically depicts a battery 60 in accordance with the invention mounted in a housing 64 (shown partially open for the purposes of illustration) of a medical device 66 configured for implanting in a patient's body. The housing 64 is preferably formed of biocompatible material and hermetically sealed. The device 66 is typically used for monitoring and/or affecting body parameters. For example, the device can be used to electrically stimulate nerves. The casing 68 of battery 64 can, for example, have dimensions of 35 mm×17 mm×5.5 mm.

While the invention has been described with reference to specific exemplary embodiments and applications, it should be recognized that numerous modifications and variations will occur to those skilled in the art without departing from the spirit and scope of the invention set forth in the appended claims.

What is claimed is:

1. A rechargeable battery comprising:
    one positive electrode, said positive electrode comprising a metal substrate having one positive active material formed thereon, said positive active material consisting of a lithium oxide comprising cobalt and nickel;
    a negative electrode comprising a metal substrate selected from the group consisting of titanium and titanium alloy having a second active material comprising carbon formed thereon;
    an electrolyte wherein said negative electrode and said electrolyte form a solid electrolyte interface (SEI) layer, said SEI layer being susceptible of damage when a voltage potential exceeding a Film Dissolution Potential (FDP) is applied thereto, and wherein said FDP is lower than the maximum positive operating potential of the battery;
    said positive and negative electrodes defining a Zero Volt Crossing Potential (ZCP) relative to a reference level when the voltage between said electrodes is zero; and wherein
    said positive and negative electrodes are selected and configured to establish ZCP at a lower level than FDP to prevent dissolution of said SEI layer during storage at a predetermined temperature.

2. The battery of claim 1 wherein said negative electrode substrate is susceptible of permanent damage when a potential exceeding a Substrate Dissolution Potential (SDP) is applied thereto; and wherein
    said positive and negative electrodes are selected and configured to establish ZCP at a lower level than SDP in order to prevent dissolution of the negative substrate during storage at said predetermined temperature.

3. The battery of claim 1 wherein said negative electrode active material consists of carbon.

4. The battery of claim 1 wherein said electrolyte consists of a liquid electrolyte.

5. The battery of claim 4 wherein said liquid electrolyte comprises a lithium salt dissolved in EC:DEC.

6. The battery of claim 5 wherein said lithium salt is $LiPF_6$.

7. The battery of claim 1 wherein said predetermined temperature is body temperature.

8. The battery of claim 1 wherein said predetermined temperature is about 37° C.

9. The battery of claim 1 wherein said predetermined temperature is about 25° C.

10. The battery of claim 1 further comprising a battery management circuit that attempts to stop battery discharge when the battery voltage reaches 2.5 V, wherein the maximum battery voltage is greater than 2.5 V.

11. The battery of claims 1 wherein said ZCP is greater than about 3 V vs. Li/Li+.

12. The battery of claim 1 wherein said positive electrode has a positive discharge curve having a negative slope over most of said positive discharge curve, wherein said negative slope is more negative than the negative slope over most of the discharge curve of $LiCoO_2$.

13. The battery of claim 1 further including a hermetically sealed case for housing said positive and negative electrodes.

14. The battery of claim 13 wherein said case is configured to be implanted in a patient's body.

15. The battery of claim 13 wherein said case has a volume of less than 30 cc.

16. A rechargeable battery comprising:
    one positive electrode, said positive electrode comprising a metal substrate having one positive active material formed thereon, said positive active material consisting of a lithium oxide comprising cobalt and nickel;
    a negative electrode comprising a substrate selected from the group consisting of titanium and titanium alloy having a second active material comprising carbon formed thereon;
    said negative electrode being susceptible of damage when a voltage exceeding a Damage Potential Threshold (DPT) is applied thereto, and wherein said DPT is lower than the maximum positive operating potential of the battery;
    said positive and negative electrodes defining a Zero Volt Crossing Potential (ZCP) relative to a reference level when the voltage between said electrodes is zero; and wherein
    said positive and negative electrodes are selected and configured to define a value of ZCP which is less than the value of DPT at a predetermined temperature.

17. The battery of claims 16 wherein the Damage Potential Threshold (DPT) is defined by a Substrate Dissolution Potential, which is the dissolution potential of the negative electrode substrate relative to said reference level.

18. The battery of claim 16 further comprising a solid electrolyte interface (SEI) formed on the negative electrode, and wherein the Damage Potential Threshold (DPT) is defined by a Film Dissolution Potential (FDP), which is the voltage above which the SEI layer begins to dissolve.

19. The battery of claim 16 wherein said predetermined temperature is body temperature.

20. The battery of claim 16 wherein said predetermined temperature is about 37° C.

21. The battery of claim 16 wherein said predetermined temperature is 25° C.

22. The battery of claim 16 further comprising a battery management circuit that attempts to stop battery discharge when the battery voltage reaches 2.5 V, wherein the maximum battery voltage is greater than 2.5 V.

23. The battery of claim 16 wherein said ZCP is greater than about 3 V vs. Li/Li+.

24. The battery of claim 16 wherein said positive electrode has a positive discharge curve having a negative slope over most of said positive discharge curve, wherein said negative slope is more negative than the negative slope over most of the discharge curve of $LiCoO_2$.

25. The battery of claim 16 wherein further including a hermetically sealed case for housing said positive and negative electrodes.

26. The battery of claim 25 wherein said case is configured to be implanted in a patient's body.

27. The battery of claim 25 wherein said case has a volume of less than 30 cc.

* * * * *